United States Patent
Jewell et al.

(10) Patent No.: US 12,083,294 B2
(45) Date of Patent: Sep. 10, 2024

(54) COUPLING BETWEEN A TELESCOPING NEEDLE SHIELD AND A CATHETER ADAPTER

(71) Applicant: Becton, Dickinson and Company, Franklin Lakes, NJ (US)

(72) Inventors: Derek Jewell, Cottonwood Heights, UT (US); Yiping Ma, Layton, UT (US); John Stokes, Pleasant View, UT (US); Chad Alan Tagge, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/793,917

(22) Filed: Feb. 18, 2020

(65) Prior Publication Data
US 2020/0261702 A1    Aug. 20, 2020

Related U.S. Application Data

(60) Provisional application No. 62/808,133, filed on Feb. 20, 2019.

(51) Int. Cl.
*A61M 25/06* (2006.01)
*A61M 25/01* (2006.01)

(52) U.S. Cl.
CPC .... *A61M 25/0618* (2013.01); *A61M 25/0606* (2013.01); *A61M 2025/0175* (2013.01)

(58) Field of Classification Search
CPC .... A61M 2039/066; A61M 2005/3226; A61M 2025/0175; A61M 25/0631; A61M 25/0618; A61M 25/0606; A61M 39/06
See application file for complete search history.

(56) References Cited

U.S. PATENT DOCUMENTS

| 5,000,740 | A | * | 3/1991 | Ducharme | A61M 25/0631 604/162 |
|---|---|---|---|---|---|
| 5,026,351 | A | * | 6/1991 | Dizon | A61M 25/0612 604/264 |

(Continued)

FOREIGN PATENT DOCUMENTS

| CN | 101573154 A | 11/2009 |
|---|---|---|
| CN | 101884823 A | 11/2010 |
| CN | 102698350 B | 9/2015 |
| CN | 106620995 A | 5/2017 |
| CN | 107205704 A | 9/2017 |

(Continued)

*Primary Examiner* — Phillip A Gray
*Assistant Examiner* — Anna E Goldberg-Richmeier
(74) *Attorney, Agent, or Firm* — Kirton McConkie; Whitney Blair; Kevin Stinger (57) ABSTRACT

A catheter system may include a catheter adapter and a needle shield device coupled to the catheter adapter. The needle shield device may include a needle housing and a needle assembly slideably coupled to the needle housing. The needle housing may include an elongated body and a nose portion coupled to the elongated body. The elongated body may include a distal end, a proximal end, and a slot disposed between the distal end and the proximal end of the elongated body. The needle assembly may include a needle grip and a needle hub having a protuberance coupled to the needle grip and slideably fit within the slot. To facilitate securement between the catheter adapter and the needle shield device, a flexible arm of the needle shield device may couple to the catheter adapter and/or multiple protrusions of the nose portion may contact an internal wall of the catheter adapter.

6 Claims, 11 Drawing Sheets

(56) References Cited

U.S. PATENT DOCUMENTS

| | | | |
|---|---|---|---|
| 5,205,829 A | | 4/1993 | Lituchy |
| 5,215,525 A | * | 6/1993 | Sturman ........... A61M 25/0631 |
| | | | 604/164.08 |
| 5,951,515 A | * | 9/1999 | Osterlind ............ A61M 25/065 |
| | | | 604/110 |
| 2007/0191776 A1 | * | 8/2007 | Bialecki ............ A61M 25/0606 |
| | | | 604/164.08 |
| 2010/0168674 A1 | * | 7/2010 | Shaw .................... A61M 39/06 |
| | | | 604/164.07 |
| 2013/0030391 A1 | * | 1/2013 | Baid ................. A61M 25/0618 |
| | | | 604/272 |
| 2016/0220791 A1 | * | 8/2016 | Akcay ............... A61B 5/150732 |
| 2017/0239443 A1 | | 8/2017 | Abitabilo et al. |

FOREIGN PATENT DOCUMENTS

| | | | |
|---|---|---|---|
| JP | 2009527285 A | 7/2009 | |
| JP | 2014533985 A | 12/2014 | |
| WO | 2007/098355 | 8/2007 | |
| WO | 2008/064332 | 5/2008 | |
| WO | WO-2008064332 A2 * | 5/2008 | ........ A61M 25/0606 |
| WO | 2013/014638 | 1/2013 | |
| WO | 2014/182421 | 11/2014 | |
| WO | 2015/115316 | 8/2015 | |
| WO | 2016/123612 | 8/2016 | |
| WO | WO-2016123612 A1 * | 8/2016 | ............ A61M 5/422 |
| WO | 2017/074684 | 5/2017 | |
| WO | 2019/018479 | 1/2019 | |
| WO | WO-2019152630 A1 * | 8/2019 | ........ A61M 25/0097 |

\* cited by examiner

COUPLING BETWEEN A TELESCOPING NEEDLE SHIELD AND A CATHETER ADAPTER

RELATED APPLICATIONS

This application claims the benefit of U.S. Provisional Application No. 62/808,133, filed on Feb. 20, 2019, and entitled COUPLING BETWEEN A TELESCOPING NEEDLE SHIELD AND A CATHETER ADAPTER which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are generally inserted at a shallow angle through the skin into vasculature of the patient.

In order to verify proper placement of the introducer needle and/or the PIVC in the blood vessel, a user generally confirms that there is "flashback" of blood in a flashback chamber of a PIVC assembly. Once placement of the needle has been confirmed, the user may temporarily occlude flow in the vasculature and remove the introducer needle, leaving the PIVC in place for future blood withdrawal and/or fluid infusion.

There is a risk of accidental needle stick if the sharp distal tip of the introducer needle is not secured properly in a needle shield or cover. Thus, the PIVC assembly may include the needle shield. When the needle shield includes a slot for telescoping between elements of the needle shield, a nose portion may be secured to a distal end of the needle shield during assembly of the PIVC assembly. The nose portion may be secured to the distal end of the needle shield after the elements are placed in a telescoping configuration. The nose portion is not configured for secure coupling between the needle shield and the catheter adapter.

In some instances, the needle shield may prematurely decouple from a catheter adapter due to a poor connection between the needle shield and the catheter adapter. Premature decoupling between the needle shield and the catheter adapter may result in the blood leaking out of the needle shield, which poses a risk of blood exposure to the user and others. Premature decoupling may also result in exposure of a sharp distal tip of the introducer needle, posing another risk to the user and others.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to needle shield devices and related devices, systems, and methods. In some embodiments, a catheter system may include a needle shield device coupled to a catheter adapter. In some embodiments, the catheter adapter may include a distal end, a proximal end, and an internal wall forming a lumen extending through the distal end of the catheter adapter and the proximal end of the catheter adapter. In some embodiments, the catheter system may include a catheter, which may include a distal end and a proximal end. In some embodiments, the catheter may include a peripheral intravenous catheter ("PIVC"). In some embodiments, the proximal end of the catheter may be secured within the catheter adapter.

In some embodiments, the needle shield device may include a needle housing. In some embodiments, the needle housing may include an elongated body, which may include a distal end, a proximal end, and a slot disposed between the distal end of the elongated body and the proximal end of the elongated body. In some embodiments, the needle housing may include a nose portion, which may be coupled to the distal end of the elongated body. In some embodiments, the nose portion may be configured to be inserted into a catheter adapter.

In some embodiments, the needle shield device may include a needle assembly, which may be slideably coupled to the needle housing. In some embodiments, the needle assembly may include an introducer needle, which may include sharp distal tip and a proximal end. In some embodiments, the needle assembly may include a needle grip and a needle hub. In some embodiments, the proximal end of the introducer needle may be secured within the needle hub.

In some embodiments, a protuberance of the needle hub may be coupled to the needle grip. In some embodiments, the protuberance may slideably fit within the slot. In some embodiments, the needle assembly may be moveable between a distal position and a proximal position with respect to the needle housing. In some embodiments, in response to movement of the needle assembly to the proximal position, the sharp distal tip may be disposed within the needle housing.

In some embodiments, the nose portion may include a plate and/or an extension extending distally from the plate. In some embodiments, the extension may include one or more protrusions (which may be referred to in the present disclosure as "extension protrusions"). In some embodiments, the extension protrusions may contact the internal wall of the catheter adapter to facilitate securement of the needle shield device to the catheter adapter during insertion of a catheter of the catheter adapter into vasculature of a patient.

In some embodiments, a maximum outer diameter of the extension may be greater than an inner diameter of the internal wall of the catheter adapter such that the extension is disposed within the catheter adapter in an interference fit. In some embodiments, the maximum outer diameter of the extension may be disposed at a location of the extension protrusions, which may interfere with the internal wall of the catheter adapter. In some embodiments, the maximum outer diameter of the extension may be disposed at a location of two opposing extension protrusions, which may interfere with the internal wall of the catheter adapter.

In some embodiments, the internal wall of the catheter adapter may include one or more other protrusions (which may be referred to in the present disclosure as "adapter protrusions"). In some embodiments, each of the adapter protrusions may contact the extension of the nose portion. In some embodiments, the adapter protrusions may be disposed proximal to the extension protrusions.

In some embodiments, the extension protrusions and/or the adapter protrusions may facilitate securement of the needle shield device to the catheter adapter during insertion of a catheter of the catheter adapter into vasculature of a patient. In some embodiments, the extension protrusions and/or the adapter protrusions may prevent or discourage premature uncoupling of the needle shield device from the catheter adapter. For example, the extension protrusions and/or the adapter protrusions may prevent or discourage uncoupling of the needle shield device from the catheter adapter prior to enclosure of the sharp distal tip of the introducer needle within the needle shield device.

In some embodiments, the catheter adapter may include a septum disposed within the lumen of the catheter adapter. In some embodiments, the extension protrusions may contact an inner surface of the septum. In some embodiments, the inner surface of the septum may include one or more other protrusions (which may be referred to in the present disclosure as "septum protrusions"). In some embodiments, the septum protrusions may contact the extension. In some embodiments, the septum protrusions may be disposed proximal to the extension protrusions. In some embodiments, the septum protrusions may facilitate securement of the needle shield device to the catheter adapter during insertion of the catheter into the vasculature of the patient.

In some embodiments, the septum may include a distal end, a proximal end, and a barrier disposed between the distal end of the septum and the proximal end of the septum. In some embodiments, the septum may include a substantially H-shaped cross-section. In some embodiments, a portion of the inner surface of the septum proximal to the barrier may include the septum protrusions.

In some embodiments, the internal wall of the catheter adapter may include one or more grooves, which may be configured to receive the extension protrusions. In some embodiments, the extension protrusions may be disposed within the grooves. In some embodiments, in response to withdrawal of the introducer needle proximally beyond the grooves, the extension protrusions may be removed from the grooves to facilitate removal of the needle assembly from a catheter assembly of the catheter system.

In some embodiments, the nose portion may include one or more capillary tubes. In some embodiments, each of the capillary tubes may include a distal opening proximate a distal opening of a needle port, which may extend through the nose portion. In some embodiments, blood that exits the distal end of the needle port may be collected within the capillary tubes to thereby prevent the blood from exiting the nose portion.

In some embodiments, the nose portion may include multiple distally-extending arms. In some embodiments, the distally-extending arms and the proximal end of the catheter adapter may be engaged in an interference fit. In some embodiments, a distal end of each of the distally-extending arms may include a flange, which may be configured to grip a rim of the proximal end of the catheter adapter. In some embodiments, an outer diameter of the proximal end of the catheter adapter may be slightly greater than an inner diameter between a flange of a first distally-extending arm and a flange of a second distally-extending arm.

In some embodiments, the needle shield device may include a flexible arm, which may be coupled to the proximal end of the catheter adapter. In some embodiments, the flexible arm may extend from the needle grip. In some embodiments, the nose portion may include a tab. In some embodiments, in response to depression of the tab, the flexible arm may be configured to release from the proximal end of the catheter adapter. In some embodiments, a distal end of the flexible arm may include a flange, which may be configured to grip the rim of the proximal end of the catheter adapter. In some embodiments, in response to depression of the tab, the flange may release from the rim of the proximal end of the catheter adapter.

In some embodiments, the tab may extend further from a longitudinal axis of the catheter system than a distal end of the needle grip and the proximal end of the catheter adapter, which may facilitate access of the tab by the user. In some embodiments, the tab may extend outwardly from the plate and/or may be generally perpendicular to the extension.

In some embodiments, the flexible arm may extend from the elongated body. In some embodiments, a proximal portion of the flexible arm may be disposed between the elongated body and the needle grip. In some embodiments, the flexible arm may be biased toward the catheter adapter. In some embodiments, in response to movement of the needle assembly to the proximal position, the flexible arm may move away from the catheter adapter to an unbiased position and may release the proximal end of the catheter adapter.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
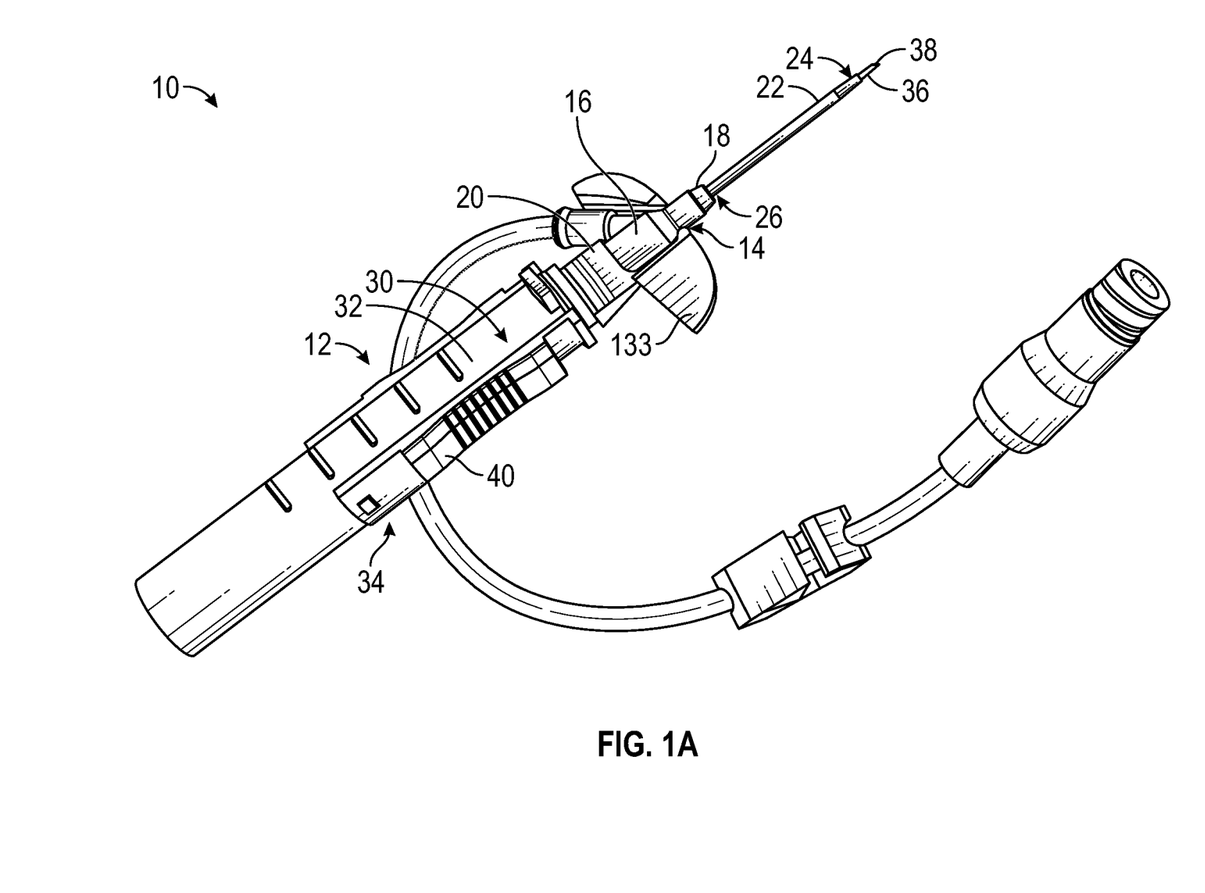
FIG. 1A is an upper perspective view of an example catheter system having an example needle shield device, according to some embodiments.

The present disclosure relates generally to needle shield devices and related devices, systems, and methods. Referring to FIG. 1A, in some embodiments, a catheter system 10 may include a needle shield device 12 and a catheter assembly 14. In some embodiments, the catheter assembly 14 may include a catheter adapter 16, which may include a distal end 18, a proximal end 20, and an internal wall forming a lumen extending through the distal end 18 and the proximal end 20. In some embodiments, the catheter assembly 14 may include a catheter 22, which may include a distal end 24 and a proximal end 26. In some embodiments, the catheter 22 may include a peripheral intravenous catheter ("PIVC") or another suitable catheter. In some embodiments, the proximal end 26 of the catheter 22 may be secured within the catheter adapter 16.

In some embodiments, the catheter system 10 may be integrated, having an integrated extension tube, such as, for example, the BD NEXIVA™ Closed IV Catheter System, the BD NEXIVA™ DIFFUSICS™ Closed IV Catheter System, the BD PEGASUS™ Safety Closed IV Catheter System, or other integrated catheter systems. An example of an integrated catheter system 10 is illustrated in FIG. 1A. In some embodiments, the catheter system 10 may be non-integrated. The catheter system 10 may include one or more features of the safety catheter assembly described in U.S. patent application Ser. No. 15/012,013, filed Feb. 1, 2016, entitled "RELEASABLE CATHETER HUB RETAINER," which is hereby incorporated by reference in its entirety.

In some embodiments, the needle shield device 12 may include a needle housing 30, which may be removably coupled to the catheter adapter 16. In some embodiments, the needle housing 30 may include an elongated body 32. In some embodiments, the needle shield device 12 may include a needle assembly 34, which may be slideably coupled to the needle housing 30.

In some embodiments, the needle assembly 34 may include an introducer needle 36, which may include sharp distal tip 38. In some embodiments, the introducer needle 36 may extend through the catheter 22 when the catheter system 10 is in an insertion position ready for insertion into vasculature of a patient, as illustrated, for example, in FIG. 1A. In some embodiments, the needle assembly 34 may include a needle grip 40, which the user may grip and move proximally to withdraw the introducer needle 36 from the vasculature once placement of the catheter 22 within the vasculature is confirmed.

In some embodiments, placement of the catheter 22 within the vasculature may be confirmed via blood flashback. In some embodiments, in response to the introducer needle 36 being inserted into the vasculature of the patient, blood flashback may flow through the sharp distal tip 38 of the introducer needle 36 and out of a distal notch of the introducer needle 36 into a portion of the catheter system 10. For example, the blood flashback may flow through the sharp distal tip 38 and out of the distal notch into a space between an exterior surface of the introducer needle 36 and an interior surface of the catheter 22.

Figure 1B:
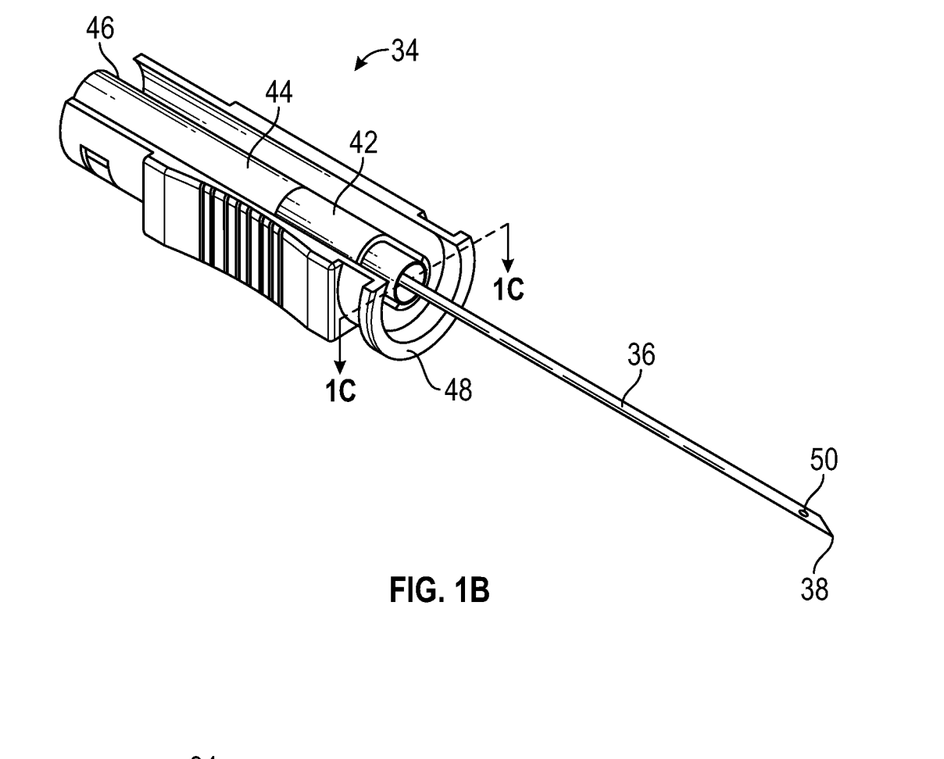
FIG. 1B is an upper perspective view of an example needle assembly of the needle shield device, according to some embodiments.

Referring now to FIG. 1B, the needle assembly 34 is illustrated, according to some embodiments. In some embodiments, the needle assembly 34 may include a needle hub 42. In some embodiments, a proximal end of the introducer needle 36 may be secured within the needle hub 42. In some embodiments, the needle hub 42 may include a flashback chamber 44. In some embodiments, in response to the introducer needle 36 being inserted into the vasculature of the patient, blood flashback may flow through the sharp distal tip 38 of the introducer needle 36 and into the flashback chamber 44. In some embodiments, at least a portion of the flashback chamber 44 and/or at least a portion of the needle housing 30 may be transparent such that the user may visualize the blood within the flashback chamber 44. In some embodiments, the flashback chamber 44 may include a material that enables air to vent from the flashback chamber 44 as blood fills the flashback chamber 44 but inhibits the blood from passing from the flashback chamber 44.

In some embodiments, the needle grip 40 may include a C-shaped cross-section configured to fit around an outer surface of the needle housing 30 in a manner that inhibits the needle hub 42 from readily separating from the needle housing 30, yet enables the needle hub 42 and needle housing 30 to slide relative to one another with minimal resistance as the needle assembly 34 moves from a distal position to a proximal position.

In some embodiments, the needle grip 40 may include one or more ridges or protrusions, which may aid in gripping of the needle grip 40 by the user. In some embodiments, the needle grip 40 may include a proximal end 46 and a distal end 48. In some embodiments, the introducer needle 36 may include a notch.

Figure 1C:
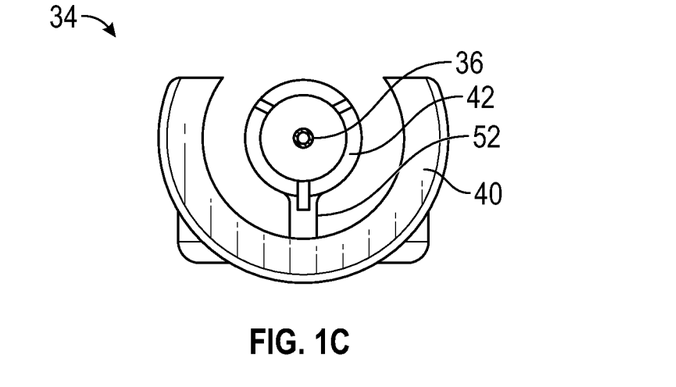
FIG. 1C is a cross-sectional view of the needle assembly along the line 1C-1C of FIG. 1B, according to some embodiments.
Figure 1D:
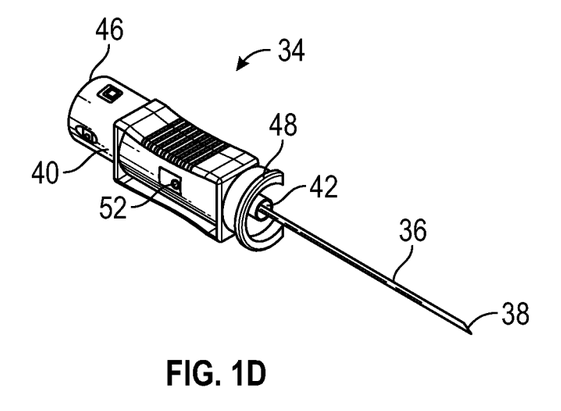
FIG. 1D is a bottom perspective view of the needle assembly, according to some embodiments.

Referring now to FIGS. 1C-1D, in some embodiments, the needle hub 42 may include a protuberance 52, which may be coupled to the needle grip 40. In some embodiments, the protuberance 52 may prevent the needle hub 42 from rotating about a longitudinal axis of the needle housing 30. In some embodiments, the needle hub 42, the protuberance 52, and the needle grip 40 may be monolithically formed as a single unit.

Figure 1E:
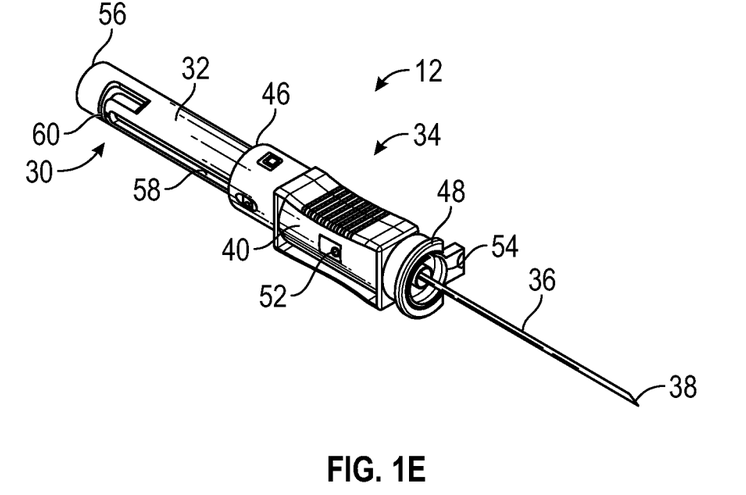
FIG. 1E is a bottom perspective view of the needle shield device in which the needle assembly is coupled to an example needle housing, illustrating the a nose portion removed and the needle assembly in a distal position with respect to the housing shield, according to some embodiments.
Figure 1F:
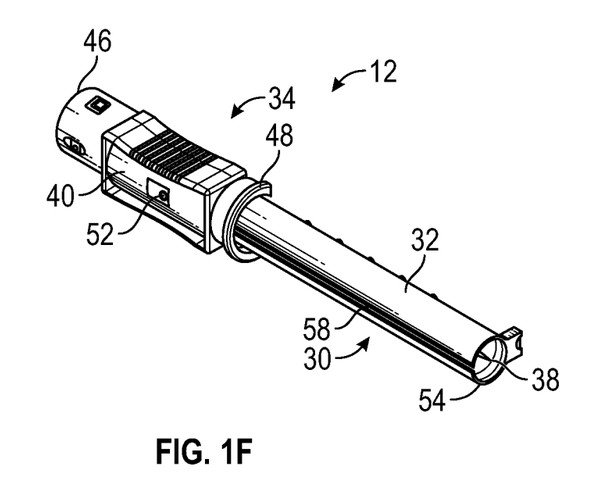
FIG. 1F is a bottom perspective view of the needle shield device, illustrating the nose portion removed and the needle assembly in a proximal position with respect to the needle housing, according to some embodiments.

Referring now to FIGS. 1E-1F, the elongated body 32 may include a distal end 54, a proximal end 56, and a slot 58 disposed between the distal end 54 and the proximal end 56. In some embodiments, the protuberance 52 may slideably fit within the slot 58. In some embodiments, the needle assembly 34 may be moveable with respect to the needle housing 30 between the distal position, illustrated, for example in FIG. 1E, and the proximal position, illustrated, for example in FIG. 1F. In some embodiments, in response to movement of the needle assembly 34 to the proximal position, the sharp distal tip 38 may be disposed within the needle housing 30, as illustrated, for example, in FIG. 1F.

In some embodiments, after positioning in the proximal or safe position, return movement of the needle assembly 34 back toward the distal or ready for use position may be inhibited by a needle lock 60. In some embodiments, the needle lock 60 may thus be configured to interlock the needle hub 42 to the needle housing 30 in the proximal position. In some embodiments, the needle lock 60 may be positioned on a proximal portion of the needle housing 30 at a proximal end of the slot 58 to engage the protuberance 52.

In some embodiments, several different types of locking mechanisms can be used for this purpose. For example, the slot 58 may include a bottleneck that may have a narrower width than a portion of the slot 58 adjacent the bottleneck. In some embodiments, the protuberance 52 of the needle hub 42 may be triangular or wedge-like in shape where an apex of the wedge faces the bottleneck when in distal position. In some embodiments, when an external force is applied to the needle hub 42 in an effort to slide it into the proximal position, the apex of the wedge of the protuberance 52 may come into contact with the bottleneck. In some embodiments, the bottleneck may include a width narrower than that of the protuberance 52 and may initially resist movement of the protuberance 52 through the bottleneck. In some embodiments, with sufficient force the protuberance 52 may cause the bottleneck to temporarily deform, thereby enabling the protuberance 52 to pass through the bottleneck to lock in the proximal position relative to the needle housing 30.

In some embodiments, the slot 58 may be disposed on a bottom of the elongated body 32, as illustrated, for example, in FIGS. 1E-1F. In some embodiments, the bottom of the elongated body 32 may face the skin of the patient when the catheter system 10 is inserted within the vasculature of the patient. In some embodiments, the slot 58 may be disposed at another location of the elongated body 32. In some embodiments, the slot 58 may be disposed on a top or side of the elongated body 32.

Referring now to FIGS. 2A-2E, in some embodiments, the needle housing 30 may include a nose portion 62, which may be coupled to the distal end 54 of the elongated body 32. In some embodiments, the nose portion 62 may be a separate piece from the elongated body 32 and may be secured to the elongated body after the protuberance 52 is disposed within the slot 58 during assembly. In some embodiments, the nose portion 62 may be configured to be inserted into the catheter adapter 16. In some embodiments, the needle housing 30 may include a septum 64 disposed within the elongated body 32 and/or the nose portion 62. In some embodiments, the septum 64 may be replaced with a membrane. In some embodiments, the catheter adapter 16 may include a septum 68.

In some embodiments, the nose portion 62 may include a plate 70 and/or an extension 72 extending distally from the plate 70. In some embodiments, the extension 72 may include one or more protrusions 74 (which may be referred to in the present disclosure as "extension protrusions"). In some embodiments, the extension protrusions 74 may contact the internal wall 76 of the catheter adapter to facilitate securement of the needle shield device 12 to the catheter assembly 14 during insertion of the catheter 22 into the vasculature of the patient.

In some embodiments, a proximal end 75 of the nose portion 62 may snugly fit within the distal end 54 of the elongated body 32 and a seal may be formed between the elongated body 32 and the proximal end 75 of the nose portion 62. In some embodiments, the plate 70 may be generally planar or curved. In some embodiments, the plate 70 may be flush with the distal end 54 of the elongated body 32. In these and other embodiments, a diameter of the plate 70 may be about equal to or slightly greater than an inner diameter of the distal end 54. In some embodiments, the diameter of the plate 70 may be greater than the diameter of the distal end 54. In some embodiments, the internal wall 76 of the extension 72 may seal with the extension 72.

In some embodiments, a maximum outer diameter 78 of the extension 72 may be greater than an inner diameter of the internal wall 76 of the catheter adapter 16 such that the extension 72 is disposed within the catheter adapter 16 in an interference fit. In some embodiments, the maximum outer diameter 78 of the extension 72 may be disposed at a location of the extension protrusions 74, which may interfere with the internal wall 76 of the catheter adapter 16. In some embodiments, the maximum outer diameter 78 of the extension 72 may be disposed at a location of two opposing extension protrusions 74, as illustrated, for example, in FIG. 2C-2D, which may interfere with the internal wall 76 of the catheter adapter 16.

Figure 2A:
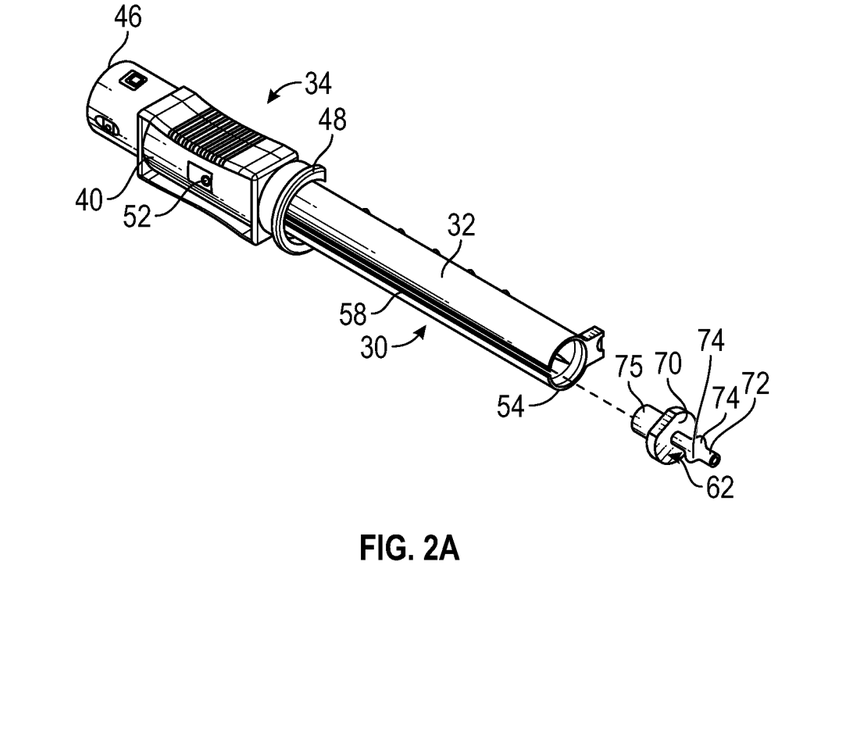
FIG. 2A is an exploded view of the needle shield device, illustrating an example nose portion that includes example extension protrusions, according to some embodiments.
Figure 2B:
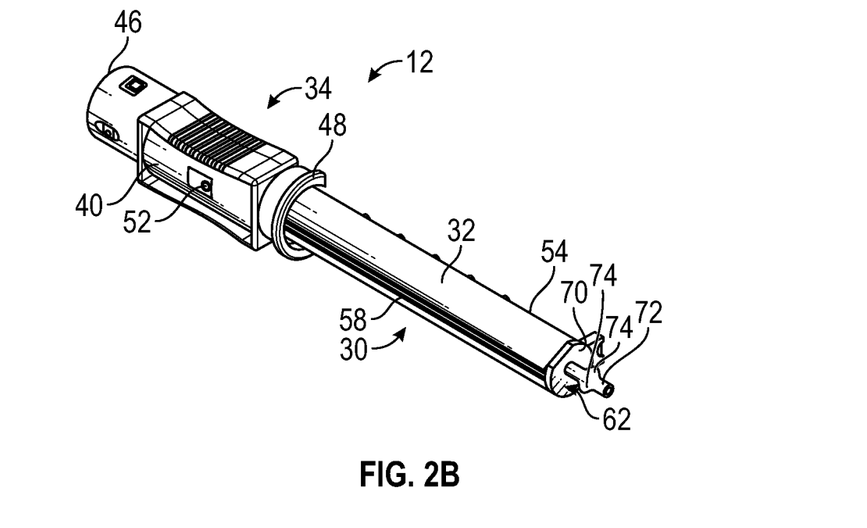
FIG. 2B is a bottom perspective view of the needle shield device, illustrating the nose portion of FIG. 2A and illustrating the needle assembly in the proximal position, according to some embodiments.
Figure 2C:
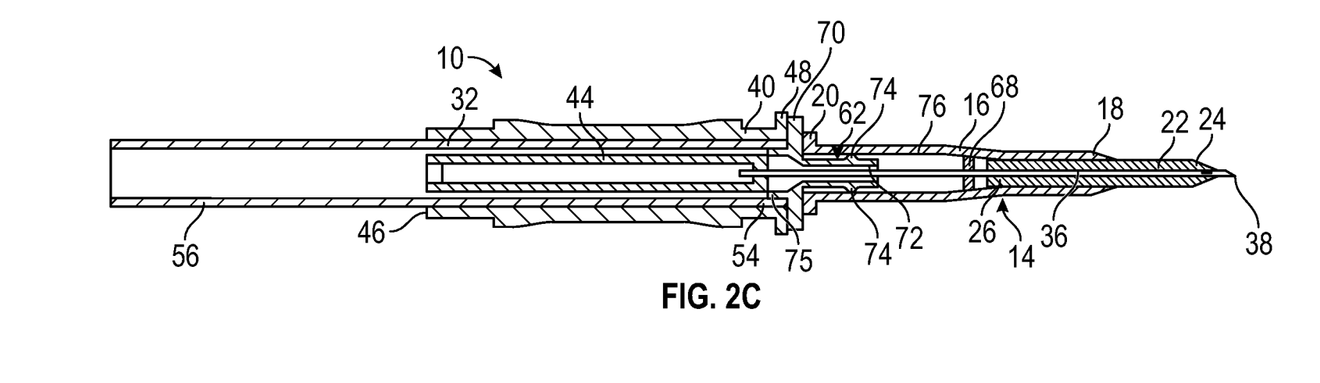
FIG. 2C is a cross-sectional view of the catheter system, illustrating the nose portion of FIG. 2A and illustrating the needle assembly in the distal position with respect to the needle housing, according to some embodiments.
Figure 2D:
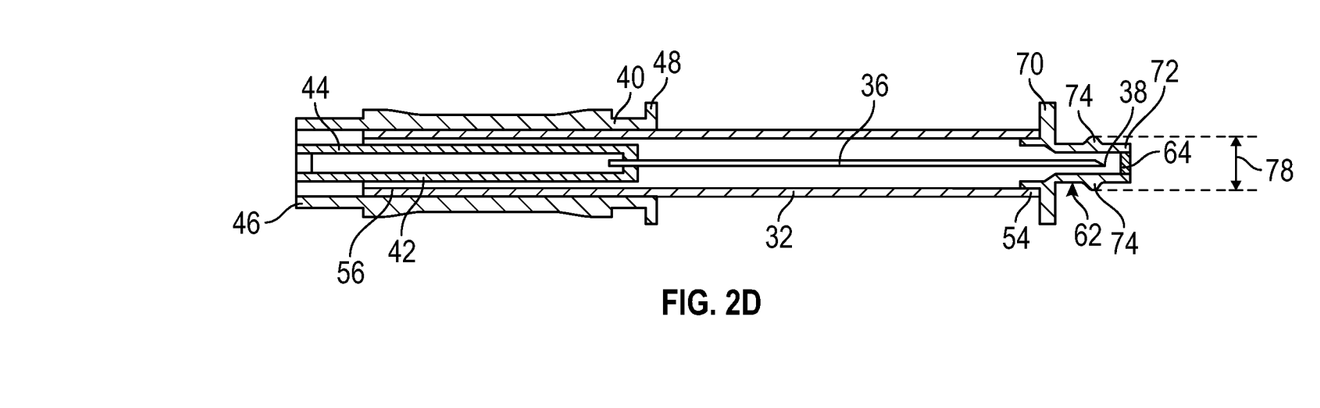
FIG. 2D is a cross-sectional view of the needle shield device, illustrating the nose portion of FIG. 2A and illustrating the needle assembly in the proximal position with respect to the needle housing, according to some embodiments.
Figure 2E:
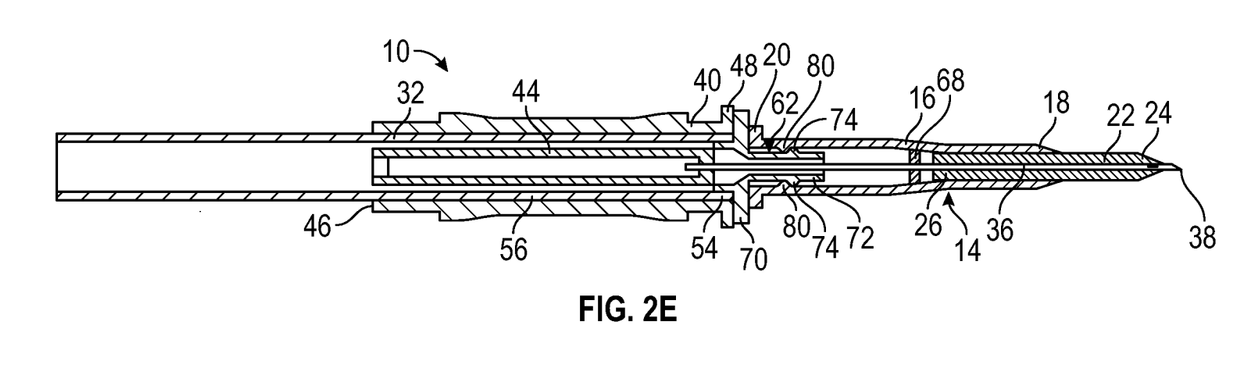
FIG. 2E is a cross-sectional view of the catheter system, illustrating the nose portion of FIG. 2A and illustrating example adapter protrusions, according to some embodiments.

As illustrated, for example, in FIG. 2E, in some embodiments, the internal wall 76 of the catheter adapter 16 may include one or more other protrusions 80 (which may be referred to in the present disclosure as "adapter protrusions"). In some embodiments, each of the adapter protrusions 80 may contact the extension 72 of the nose portion 62. In some embodiments, the adapter protrusions 80 may be disposed proximal to the extension protrusions 74 and may provide resistance in response to proximal movement of the nose portion 62.

In some embodiments, the extension protrusions 74 and/or the adapter protrusions 80 may facilitate securement of the needle shield device 12 to the catheter adapter 16 during insertion of the catheter 22 and the introducer needle 36 into the vasculature of the patient. In some embodiments, the extension protrusions 74 and/or the adapter protrusions 80 may prevent or discourage premature uncoupling of the needle shield device 12 from the catheter adapter 16. For example, the extension protrusions 74 and/or the adapter protrusions 80 may prevent or discourage uncoupling of the needle shield device 12 from the catheter adapter 16 prior to enclosure of the sharp distal tip 38 of the introducer needle 36 within the needle shield device 12.

Figure 3A:
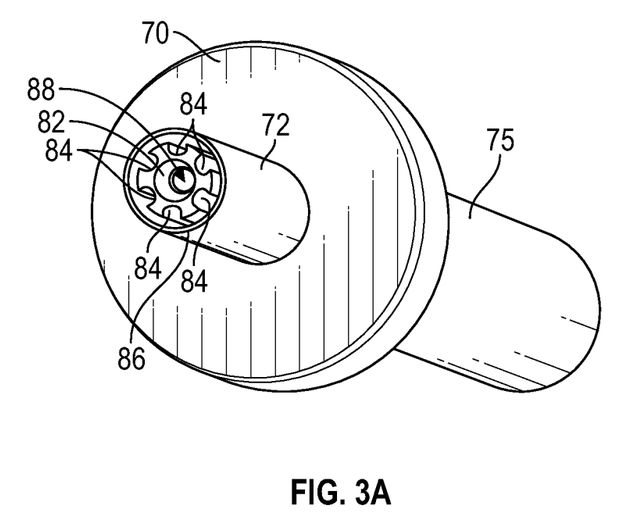
FIG. 3A is an upper perspective view of another example nose portion, according to some embodiments.
Figure 3B:
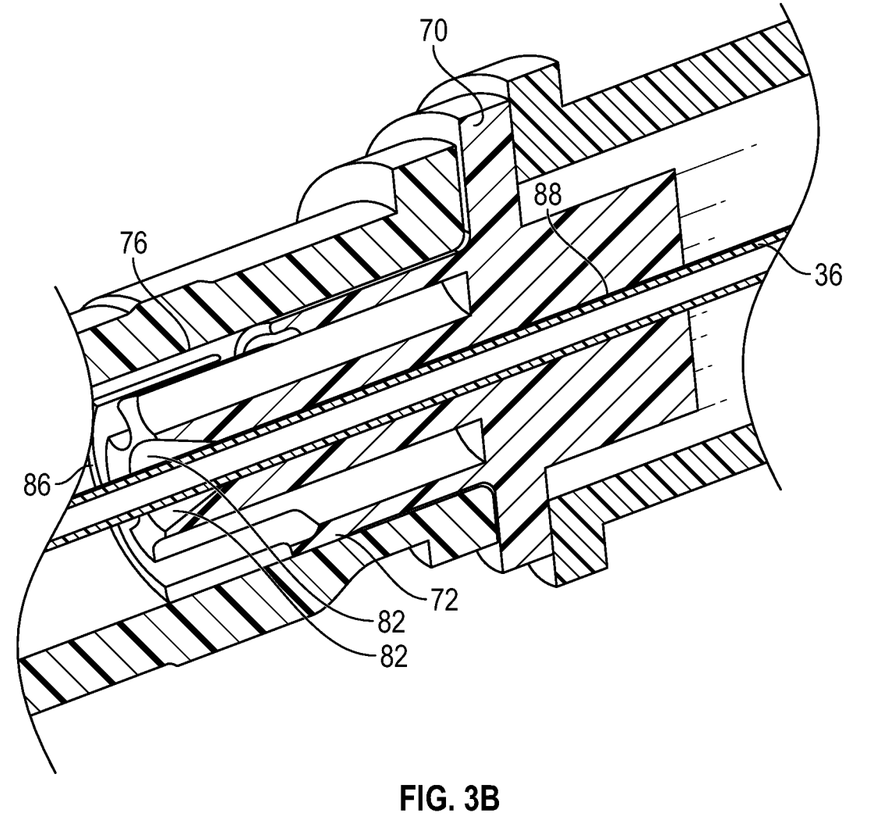
FIG. 3B is an enlarged cross-sectional view of the nose portion of FIG. 3A coupled to an example catheter adapter, according to some embodiments.

Referring now to FIGS. 3A-3B, in some embodiments, the nose portion may include one or more capillary tubes. In some embodiments, each of the capillary tubes may include a distal opening proximate a distal opening of a needle port, which may extend through the nose portion. In some embodiments, blood that exits the distal end of the needle port may be collected within the capillary tubes to thereby prevent the blood from exiting the nose portion.

In some instances, the nose portion 62 and the needle shield device 12 may be eventually removed from the catheter adapter 16, providing an opportunity for the blood in, on, and/or around the nose portion 62 to spill and potentially contaminate and/or harm the user. In some embodiments, the nose portion 62 may include a distal vent 82, which may include a space through which blood travels through the nose portion 62. In some embodiments, one or more capillary tubes 84 may be formed within the nose portion 62 in order to retain, via surface tension, the blood that comes into contact with the nose portion 62 after the nose portion 62 is disengaged from the catheter adapter 16.

In some embodiments, when the needle shield device 12 is coupled to the catheter adapter 16, the capillary tubes 84 may be surrounded by a seal surface 86 that may come into contact with the catheter adapter 16 in order to ensure that blood does not leak between the seal surface 86 and the catheter adapter 16. Thus, blood will travel from the interior of the catheter adapter 16 and into the capillary tubes 84 and the distal vent 82 between the introducer needle 36 and the interior surface of a needle port 88 within the nose portion 62. In some embodiments, as blood travels through the catheter adapter 16 and into the nose portion 62, the process of capillary action will draw blood into the capillary tubes 84.

In some embodiments, the nose portion 62 may include six capillary tubes 84. In some embodiments, the nose portion 62 may include less than six capillary tubes 84 or more than six capillary tubes 84. In some embodiments, the capillary tubes 84 may include any material and/or configuration of material beneficial in preventing unintended exposure to blood or other liquids where unintended exposure is undesirable. For example, the capillary tubes 84 may include tubes molded within the material of the nose portion 62. However, in another embodiment the capillary tubes 84 may include a configuration of fibrous materials having wicking properties wherein the fibrous materials are positioned such that upon separation of the nose portion 62 from the catheter assembly 14, the fibrous materials absorb and/or retain any residual liquids not contained within the nose portion 62 and/or the catheter adapter 16.

In some embodiments, the capillary tubes 84 may surround the distal vent 82 through which blood may travel through the nose portion 62. In some embodiments, the sealing surface 86 may interface with the internal wall 76 of the catheter adapter 16. In some embodiments, the sealing surface 86 may include a smooth surface to which the interior surface of the catheter adapter 16 may seal in order to ensure that no air or blood travels in between the interior surface of the catheter adapter 16 and the sealing surface 86.

Figure 4:
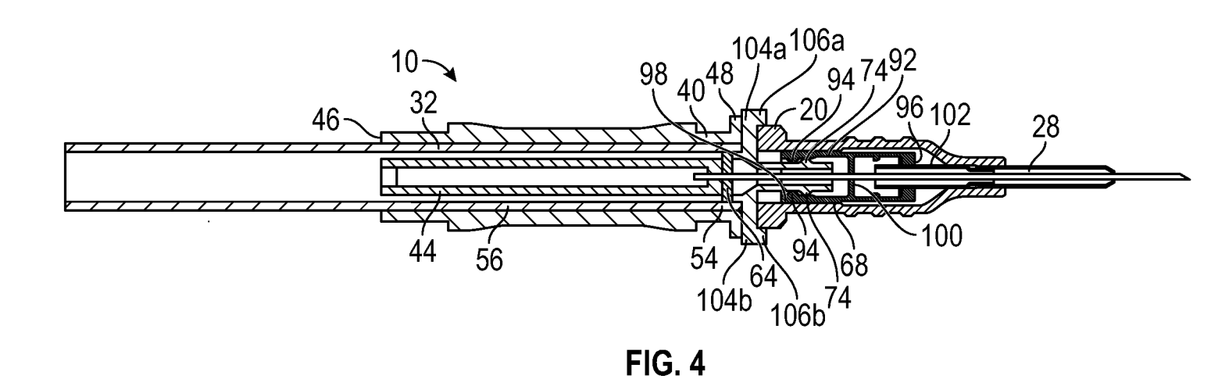
FIG. 4 is a cross-sectional view of the catheter system, illustrating example septum protrusions and example distally-extending arms, according to some embodiments.

Referring now to FIG. 4, in some embodiments, the catheter adapter 16 may include a septum 68 disposed within the lumen 90 of the catheter adapter 16. In some embodiments, the extension protrusions 74 may contact an inner surface 92 of the septum 68. In some embodiments, the inner surface 92 of the septum 68 may include one or more other protrusions 94 (which may be referred to in the present disclosure as "septum protrusions"). In some embodiments, the septum protrusions 94 may contact the extension 72. In some embodiments, the septum protrusions 94 may be disposed proximal to the extension protrusions 74 and may provide resistance in response to proximal movement of the nose portion 62. In some embodiments, the septum protrusions 94 may facilitate securement of the needle shield device 12 to the catheter adapter 16 during insertion of the catheter 22 into the vasculature of the patient.

In some embodiments, the septum 68 may include a distal end 96, a proximal end 98, and a barrier 100 disposed between the distal end 96 and the proximal end 98. In some embodiments, the barrier 100 may include a slit. In some embodiments, the septum 68 may include a substantially H-shaped cross-section. In some embodiments, a portion of the inner surface 92 of the septum 68 proximal to the barrier 100 may include the septum protrusions 94.

In some embodiments, a septum actuator 102 may be fixed within the lumen 90 of the catheter adapter 16. In some embodiments, the septum actuator 102 may be connected to a catheter 28. In some embodiments, the septum 68 may be configured to move between a proximal position and a distal position in response to insertion of a separate device into the proximal end 20 of the catheter adapter 16, after the needle shield device 12 is removed from the catheter adapter 16. In some embodiments, the septum actuator 102 may penetrate the slit in response to movement of the septum 68 from the proximal position to the distal position.

In some embodiments, the nose portion 62 may include one or more distally-extending arms. In some embodiments, the distally-extending arms 104 and the proximal end 20 of the catheter adapter 16 may be engaged in an interference fit. In some embodiments, the distally-extending arms may include a first distally-extending arm 104a and a second distally-extending arm 104b. In some embodiments, a distal end of each of the first distally-extending arm 104a and the second distally-extending arm 104b may include a first flange 106a and a second flange 106b, respectively, which may be configured to grip the proximal end 20 of the catheter adapter 16. In some embodiments, an outer diameter of the proximal end 20 of the catheter adapter 16 may be slightly greater than an inner diameter between the first flange 106a and the second flange 106b. In some embodiments, the distally-extending arms may facilitate securement of the needle shield device 12 to the catheter adapter 16 during insertion of the catheter 22 into the vasculature of the patient.

Although illustrated together, it is understood that in some embodiments, the distally-extending arms may be present without the septum protrusions 94 and/or the extension protrusions 74. In some embodiments, the septum protrusions 94 and/or the extension protrusions 74 may be present without the distally-extending arms.

Figure 5A:
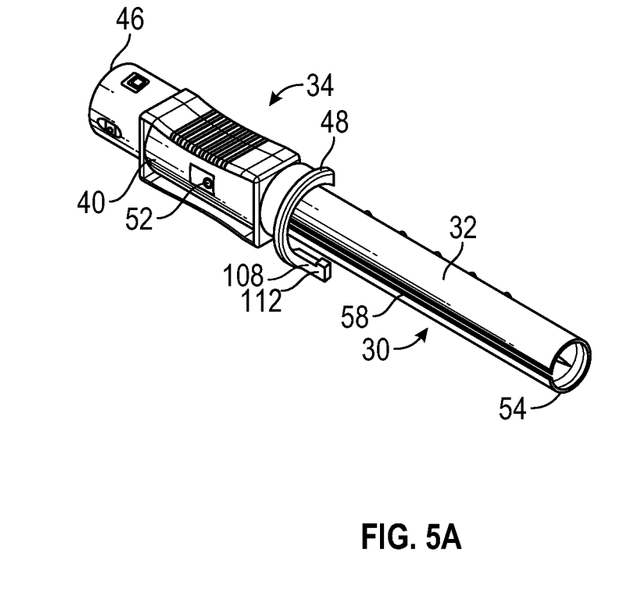
FIG. 5A is an exploded view of the needle shield device, illustrating an example flexible arm, according to some embodiments.
Figure 5B:
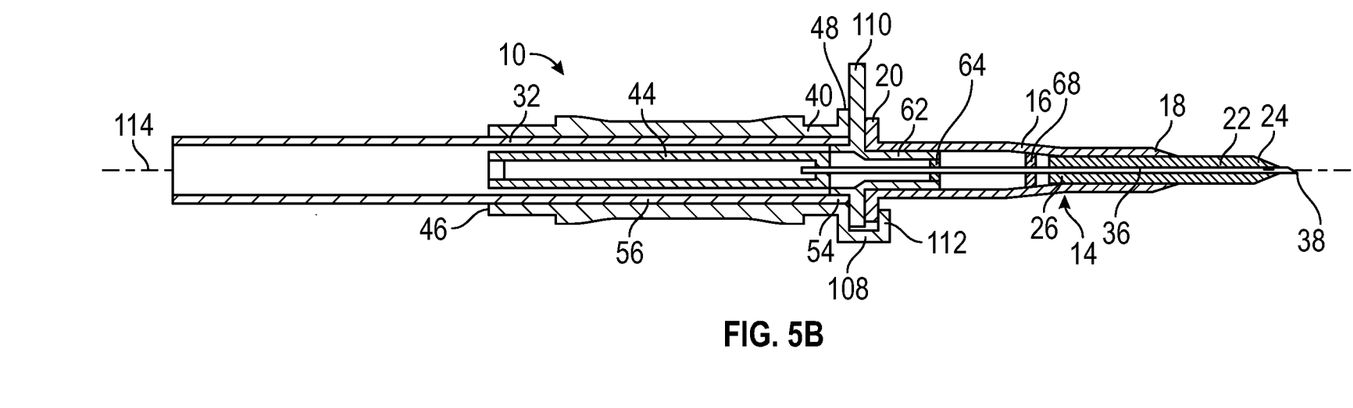
FIG. 5B is a cross-sectional view of the catheter system, illustrating the flexible arm of FIG. 5A and illustrating the needle assembly in the distal position, according to some embodiments.

In some embodiments, the needle shield device 12 may include a flexible arm 108, which may be coupled to the proximal end 20 of the catheter adapter 16. In some embodiments, the flexible arm 108 may extend from the needle grip 40. In some embodiments, the nose portion 62 may include a tab 110. In some embodiments, in response to depression of the tab 110, the flexible arm 108 may be configured to release from the proximal end 20 of the catheter adapter 16, as illustrated, for example, in FIG. 5C. In some embodiments, a distal end of the flexible arm 108 may include a flange 112, which may be configured to grip a rim of the proximal end 20 of the catheter adapter 16. In some embodiments, in response to depression of the tab 110, the nose portion 62 may contact the flexible arm 108 and/or move the flexible arm 108 away from a longitudinal axis 114 of the catheter system 10. In some embodiments, in response to depression of the tab 110, the flange 112 may release from the rim of the proximal end 20 of the catheter adapter 16.

Figure 5C:
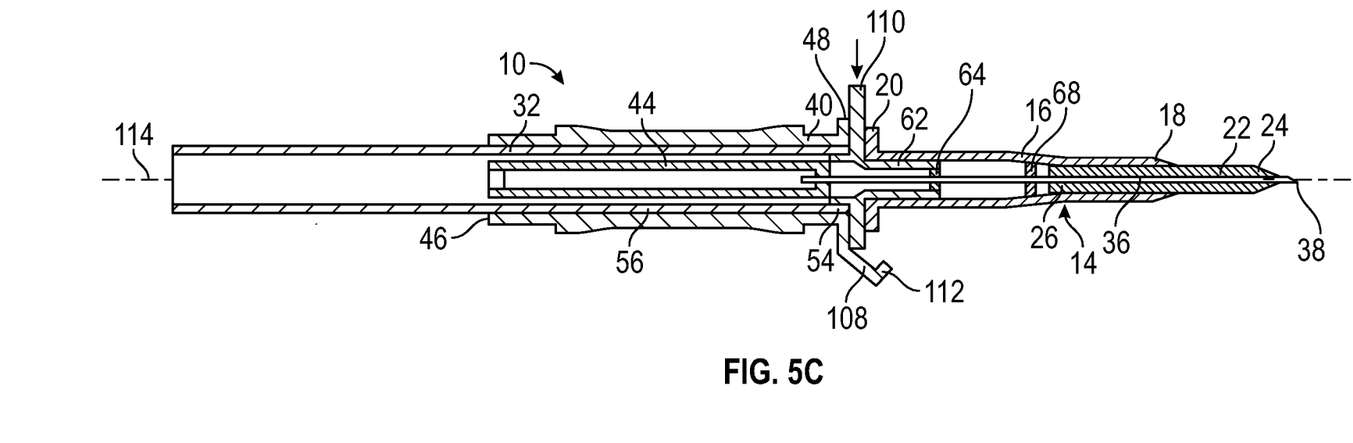
FIG. 5C is a cross-sectional view of the catheter system, illustrating the flexible arm of FIG. 5A biased outwardly, according to some embodiments.

In some embodiments, the tab 110 may extend further from the longitudinal axis 114 of the catheter system 10 than the distal end 48 of the needle grip 40 and the proximal end 20 of the catheter adapter 16, which may facilitate access of the tab 110 by the user. In some embodiments, the tab 110 may extend outwardly from the plate 70 and/or may be generally perpendicular to the extension 72.

Figure 6A:
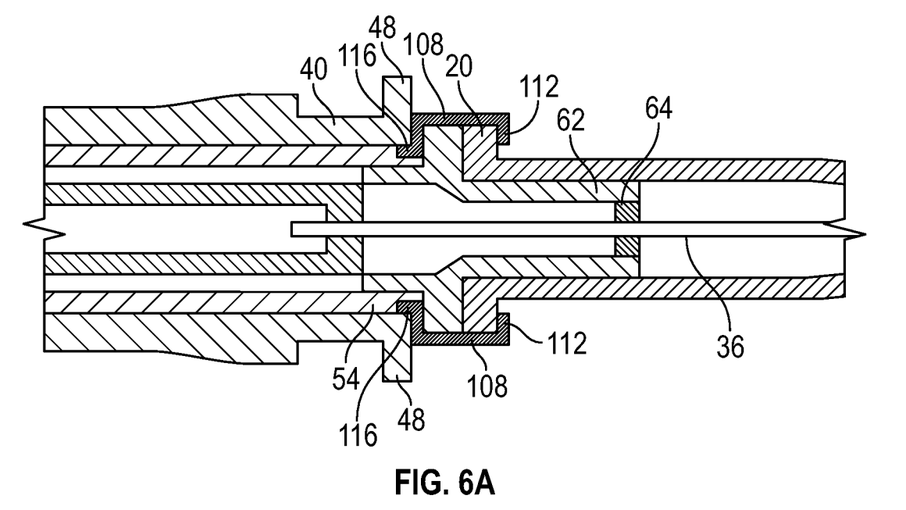
FIG. 6A is an enlarged cross-sectional view of a portion of the catheter system, illustrating another flexible arm and illustrating the needle assembly in the distal position, according to some embodiments.
Figure 6B:
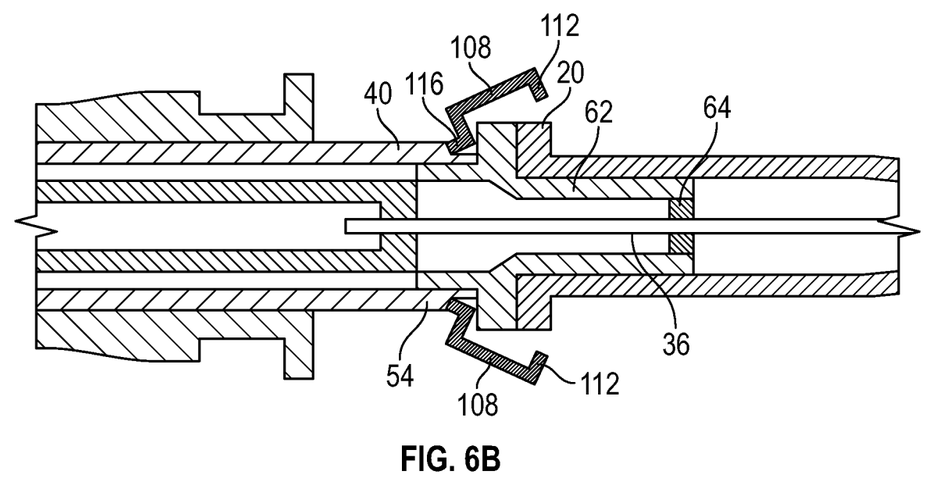
FIG. 6B is an enlarged cross-sectional view of the portion of the catheter system, illustrating the flexible arm of FIG. 6A biased outwardly, according to some embodiments.

Referring now to FIGS. 6A-6B, in some embodiments, the flexible arm 108 may extend from the elongated body 32. In some embodiments, a proximal portion 116 of the flexible arm 108 may be disposed between the elongated body 32 and the needle grip 40. In some embodiments, the flexible arm 108 may be biased toward the catheter adapter 16. In some embodiments, in response to movement of the needle assembly 34 to the proximal position, the flexible arm 108 may move away from the catheter adapter 16 to an unbiased position and may release the proximal end 20 of the catheter adapter 16, as illustrated, for example, in FIG. 6B.

Figure 7A:
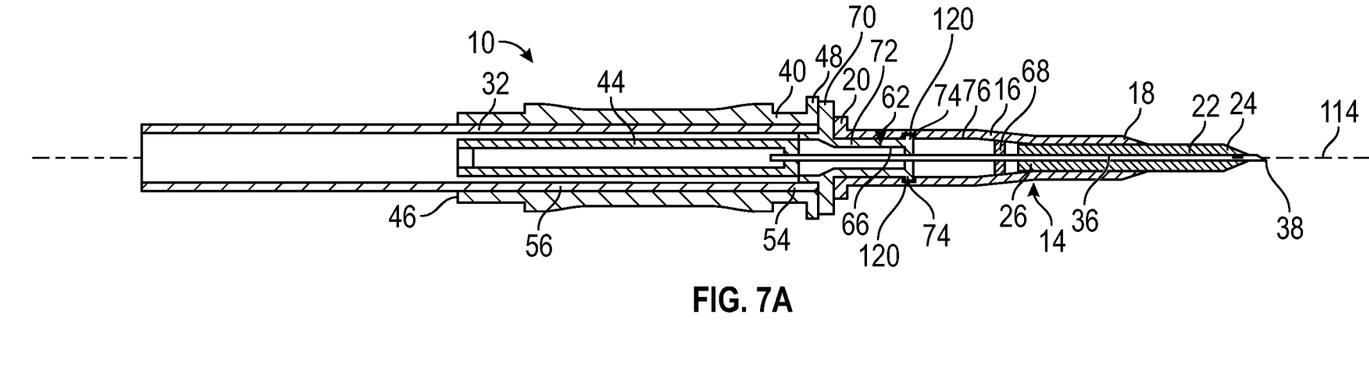
FIG. 7A is a cross-sectional view of the catheter system, illustrating example grooves disposed within the catheter adapter, according to some embodiments.
Figure 7B:
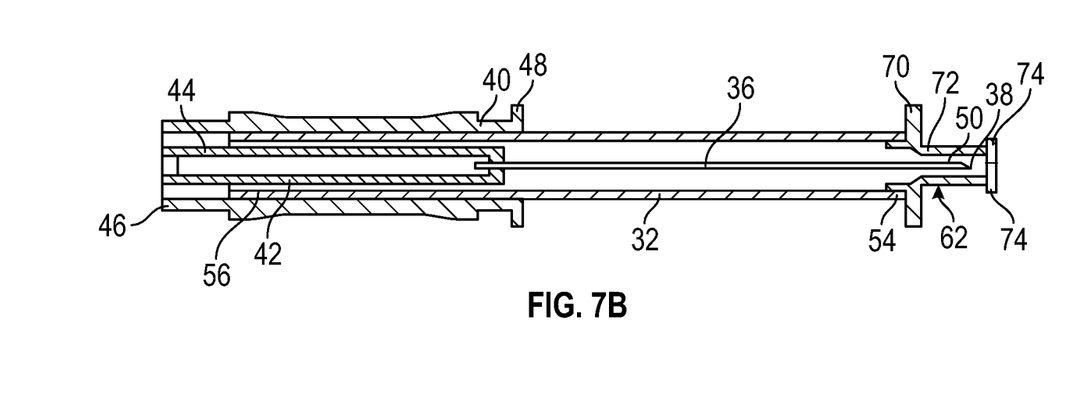
FIG. 7B is a cross-sectional view of the needle shield device, illustrating the extension protrusions removed from the grooves of FIG. 7A, according to some embodiments.

Referring now to FIGS. 7A-7B, in some embodiments, the internal wall 76 of the catheter adapter 16 may include one or more grooves 120, which may be configured to receive the extension protrusions 74. In some embodiments, the extension protrusions 74 may be disposed within the grooves 120 to facilitate securement of the needle shield device 12 to the catheter adapter 16. In some embodiments, in response to withdrawal of the introducer needle 36 proximally beyond the grooves 120, the extension protrusions 74 may move towards the longitudinal axis 114 and may be removed from the grooves 108 to facilitate removal of the needle assembly 34 from the catheter assembly 14.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
a catheter adapter, comprising a distal end, a proximal end, and an internal wall forming a lumen extending through the distal end of the catheter adapter and the proximal end of the catheter adapter; and
a needle shield device coupled to the catheter adapter, the needle shield device comprising:
a needle housing, comprising:
an elongated body having a distal end, a proximal end, and a slot disposed between the distal end of the elongated body and the proximal end of the elongated body; and
a nose portion coupled to the distal end of the elongated body, wherein the nose portion comprises a plate and an extension, wherein the extension is inserted into the catheter adapter, wherein the extension comprises a cylindrical shape extending distally from the plate to a distal end of the extension, wherein the extension further comprises two protrusions on opposite sides of the cylindrical shape and spaced apart from the plate and the distal end of the cylindrical shape, wherein each of the two protrusions contacts a portion of the internal wall of the catheter adapter, wherein when the needle housing is disconnected from the catheter adapter, a maximum outer diameter of the extension is disposed at the two protrusions and is greater than an inner diameter of the portion of the internal wall of the catheter adapter contacting the two protrusions such that the extension is disposed within the catheter adapter in an interference fit when the needle housing is coupled to the catheter adapter, wherein a surface of the portion of the internal wall of the catheter adapter contacting the two protrusions and extending through the proximal end of the catheter adapter is smooth;
a needle assembly slideably coupled to the needle housing, comprising:
an introducer needle comprising a sharp distal tip and a proximal end;
a needle grip; and
a needle hub having a protuberance, wherein the proximal end of the introducer needle is secured within the needle hub, wherein the protuberance is coupled to the needle grip, wherein the protuberance slideably fits within the slot, wherein the needle grip partially surrounds the needle housing such that the needle hub and the needle housing are configured to slide relative to each other, wherein the needle assembly is moveable between a distal position and a proximal position with respect to the needle housing, wherein in response to movement of the needle assembly to the proximal position, the sharp distal tip is disposed within the needle housing.

2. The catheter system of claim 1, wherein the nose portion comprises a plurality of capillary tubes, wherein each of the capillary tubes comprises a distal opening proximate a distal opening of a needle port extending through the nose portion such that blood that exits the distal end of the needle port is collected within the capillary tubes to thereby prevent the blood from exiting the nose portion.

3. The catheter system of claim 1, wherein the nose portion comprises a plurality of distally-extending arms, wherein the distally-extending arms and the proximal end of the catheter adapter are engaged in an interference fit.

4. The catheter system of claim 1, wherein the needle grip comprises a C-shaped cross-section.

5. A catheter system, comprising:
a catheter adapter, comprising a distal end, a proximal end, and an internal wall forming a lumen extending through the distal end of the catheter adapter and the proximal end of the catheter adapter; and
a needle shield device coupled to the catheter adapter, the needle shield device comprising:
a needle housing, comprising:
an elongated body having a distal end, a proximal end, and a slot disposed between the distal end of the elongated body and the proximal end of the elongated body; and
a nose portion coupled to the distal end of the elongated body and extending into the lumen of the catheter adapter, wherein the nose portion comprises a plate and an extension extending distally from the plate, wherein the plate covers the distal end of the elongated body and is proximate the slot;

a needle assembly slideably coupled to the needle housing, comprising:
  an introducer needle comprising a sharp distal tip and a proximal end;
  a needle grip; and
  a needle hub having a protuberance, wherein the proximal end of the introducer needle is secured within the needle hub, wherein the protuberance is coupled to the needle grip, wherein the protuberance slideably fits within the slot, wherein the needle grip partially surrounds the needle housing such that the needle hub and the needle housing are configured to slide relative to each other, wherein the needle assembly is moveable between a distal position and a proximal position with respect to the needle housing, wherein in response to movement of the needle assembly to the proximal position, the sharp distal tip is disposed within the needle housing,
wherein the needle shield device comprises a flexible arm coupled to the proximal end of the catheter adapter, wherein the flexible arm extends from the needle grip, wherein the nose portion comprises a tab extending from the plate, wherein the tab is radially opposite the flexible arm with respect to a longitudinal axis of the catheter system, wherein in response to depression of the tab, the plate is configured to contact the flexible arm opposite the tab such that the flexible arm is released from the proximal end of the catheter adapter.

6. The catheter system of claim 5, wherein the tab extends further from the longitudinal axis of the catheter system than a distal end of the needle grip and the proximal end of the catheter adapter to facilitate access of the tab by a user.

\* \* \* \* \*